United States Patent
Morris et al.

(10) Patent No.: US 9,700,699 B2
(45) Date of Patent: Jul. 11, 2017

(54) MODULAR HANDLE ASSEMBLY FOR A STEERABLE CATHETER

(71) Applicant: Freudenberg Medical, LLC, Carpinteria, CA (US)

(72) Inventors: Ben Morris, Jeffersonville, IN (US); Brian Keith Wells, La Grange, IN (US); Adwait Kumar, Prospect, KY (US); Anthony Appling, Crestwood, KY (US)

(73) Assignee: FREUDENBERG MEDICAL, LLC, Carpinteria, CA (US)

( * ) Notice: Subject to any disclaimer, the term of this patent is extended or adjusted under 35 U.S.C. 154(b) by 195 days.

(21) Appl. No.: 14/485,595

(22) Filed: Sep. 12, 2014

(65) Prior Publication Data

US 2016/0074624 A1    Mar. 17, 2016

(51) Int. Cl.
*A61M 25/01*   (2006.01)

(52) U.S. Cl.
CPC .... *A61M 25/0136* (2013.01); *A61M 25/0147* (2013.01)

(58) Field of Classification Search
CPC .......... A61M 25/0136; A61M 25/0147; A61M 2025/09116
See application file for complete search history.

(56) References Cited

U.S. PATENT DOCUMENTS

| | | | |
|---|---|---|---|
| 6,464,645 B1 * | 10/2002 | Park | A61B 1/0052 600/462 |
| 6,522,933 B2 | 2/2003 | Nguyen | |
| 2006/0100640 A1 | 5/2006 | Bolduc | |
| 2008/0065011 A1 * | 3/2008 | Marchand | A61F 2/2433 604/103.02 |
| 2008/0103520 A1 | 5/2008 | Selkee | |
| 2013/0184642 A1 | 7/2013 | O'Donnell et al. | |

FOREIGN PATENT DOCUMENTS

| | | |
|---|---|---|
| EP | 2397108 A2 | 12/2011 |
| EP | 2438954 A1 | 4/2012 |
| WO | WO9833429 A2 | 8/1998 |
| WO | 2013190475 A2 | 12/2013 |

OTHER PUBLICATIONS

European Search Report dated Jan. 28, 2016 in corresponding European Patent Application No. 15182409.1.

* cited by examiner

*Primary Examiner* — Laura Bouchelle
*Assistant Examiner* — Justin L Zamory
(74) *Attorney, Agent, or Firm* — Dickinson Wright PLLC

(57) ABSTRACT

A modular handle assembly for supporting and controlling a steerable catheter having at least one deflection wires includes a handle extending along an axis for being secured about a portion of the steerable catheter. The modular handle assembly includes at least one barrel rotatably connected to the handle for rotation about the axis, and at least one spindle disposed in and connected with said barrel for rotation about the axis with the barrel. At least one guide cable extends from an anchored end being anchored to the spindle to a distant end for connection with one of the deflection wires of the steerable catheter. The guide cable is wrapped about the spindle for axially moving the deflection wires in response to rotation of the first spindle about the axis by the barrel to curl the distal tip of the elongated body of the steerable catheter.

19 Claims, 6 Drawing Sheets

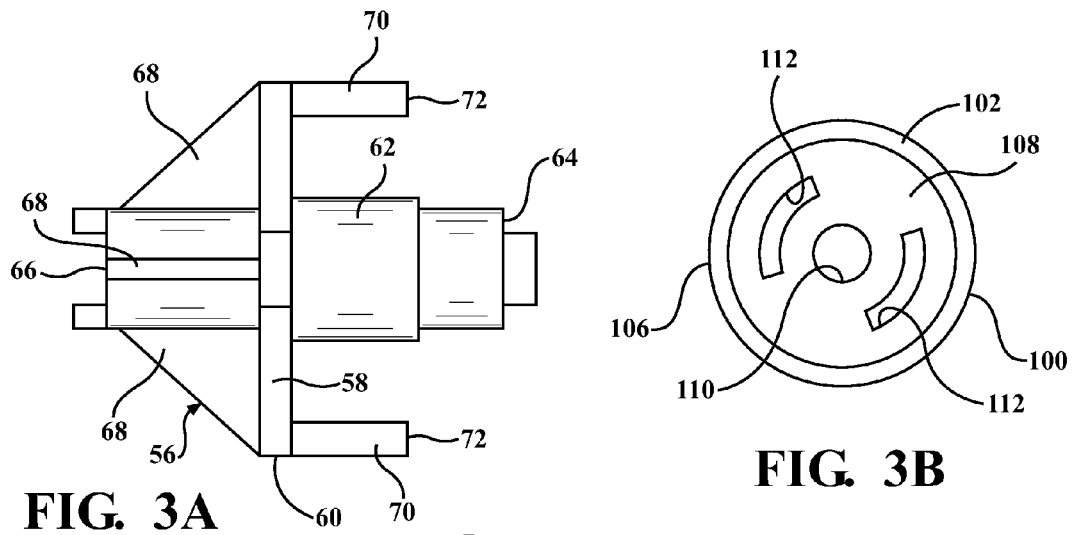
FIG. 3A
FIG. 3B
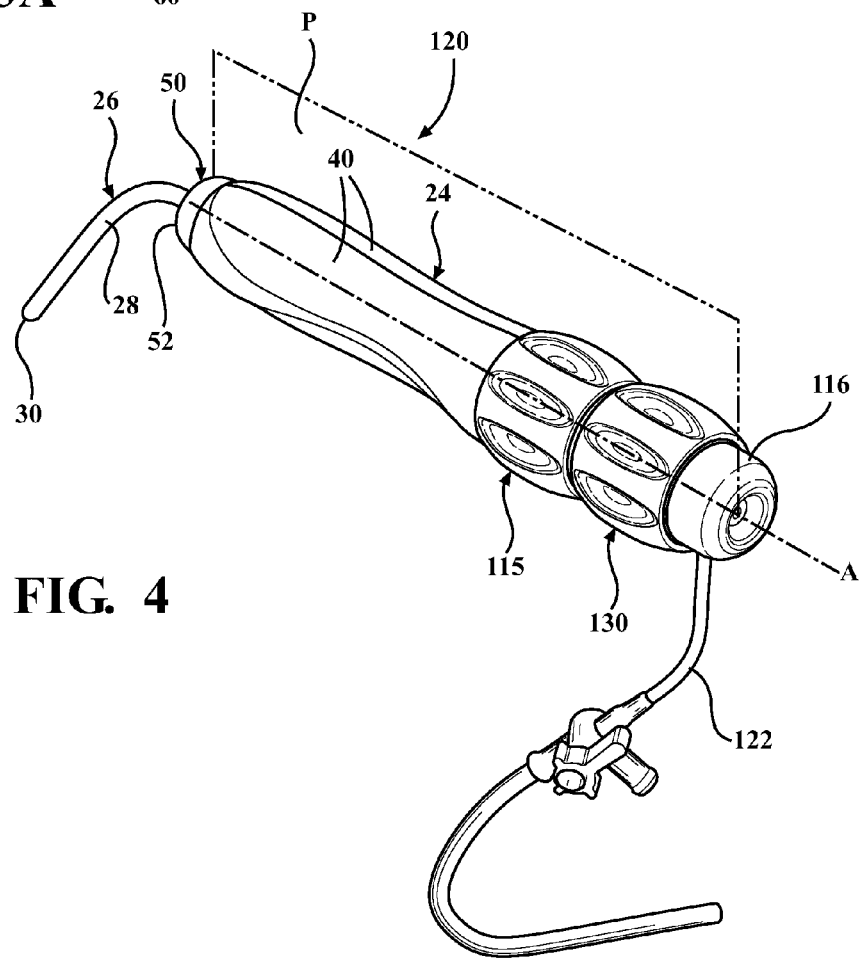
FIG. 4

MODULAR HANDLE ASSEMBLY FOR A STEERABLE CATHETER

BACKGROUND OF THE INVENTION

1. Field of the Invention

The present invention relates to steerable catheters, and more particularly to a modular handle assembly for supporting and controlling a steerable catheter.

2. Description of the Prior Art

This section provides background information related to the present disclosure which is not necessarily prior art.

Catheters (i.e., catheters or sheaths) that have flexible tubular bodies with deflectable distal ends and control handles for controlling distal end deflection are used for many non-invasive medical producers. The distal portion of the catheter body is selectively deformed into a variety of curved configurations using an actuator on the control handle which remains outside the patient's body. The actuator is commonly internally linked to the distal portion of the catheter body by at least one deflection wire. Some catheter bodies employ a single deflection wire, which is pulled (i.e., placed in tension) by the actuator in order to cause the distal portion of the catheter body to deform. Other catheter bodies have at least two deflection wires, where the displacement of one wire (i.e., placing one wire in tension) results in the other wire going slack (i.e., the wire does not carry a compressive load). In such catheters, where the deflection wires are not adapted to carry compressive loads (i.e., the deflection wires are only meant to be placed in tension), the deflection wires are commonly called pull or tension wires.

Although the prior art control handles are capable of controlling distal end deflection of catheter bodies, they have several drawbacks. For example, the prior art control handles are often excessively bulky and oftentimes expensive. Additionally, the prior art control handles often have a mechanical component that requires a significant effort to operate on the part of the user, and once a desired distal end deflection has been reached, the control handles typically require the operator to take a conscious step to maintain the catheter at the desired deflection. Further, the prior art control handles cannot be easily modified, and thus are only designed to work with a specific steerable catheter design.

Accordingly, there remains a need in the art for an improved control handle for use with a steerable catheter.

SUMMARY OF THE DISCLOSURE

This section provides a general summary of the disclosure and is not intended to be a comprehensive disclosure of its full scope, aspects, objectives, and/or all of its features.

A modular handle assembly for supporting and controlling a steerable catheter includes a handle extending along an axis for being secured about a portion of the steerable catheter. The modular handle assembly includes at least one barrel rotatably connected to the handle for rotation about the axis and at least one spindle disposed in and connected with the barrel for rotation about the axis with the barrel. The modular handle assembly further includes at least one guide cable extending from an anchored end being anchored to the spindle to a distant end for connection with one of the deflection wires of the steerable catheter. The guide cable is wrapped about the spindle for axially moving the deflection wires in response to rotation of the first spindle about the axis by way of the barrel to curl the distal tip of the elongated body of the steerable catheter.

As will be described in more detail below, the subject modular handle assembly provides for equal or better steering performance of steerable catheters using less overall parts and a simpler design than the prior art handle assemblies. Accordingly, the subject modular handle assembly provides for a lower cost solution to steering a catheter. Additionally, the subject modular handle assembly is easily customizable to achieve two or four direction deflection of the distal end of the steerable catheter, and even customizable for use with a variety of different steerable catheter designs. Thus, the subject modular handle provides for increased flexibility and modularity over the prior art handle assemblies.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

Other advantages of the present invention will be readily appreciated, as the same becomes better understood by reference to the following detailed description when considered in connection with the accompanying drawings wherein:

FIG. 3A is a magnified side view of a frame of FIG. 3;

FIG. 3B is a magnified end view of a spindle of FIG. 3;

FIG. 4 is a perspective assembled view of a second embodiment of the modular handle assembled constructed in accordance with the principles of the present disclosure;

DETAILED DESCRIPTION OF THE ENABLING EMBODIMENTS

Figure 1:
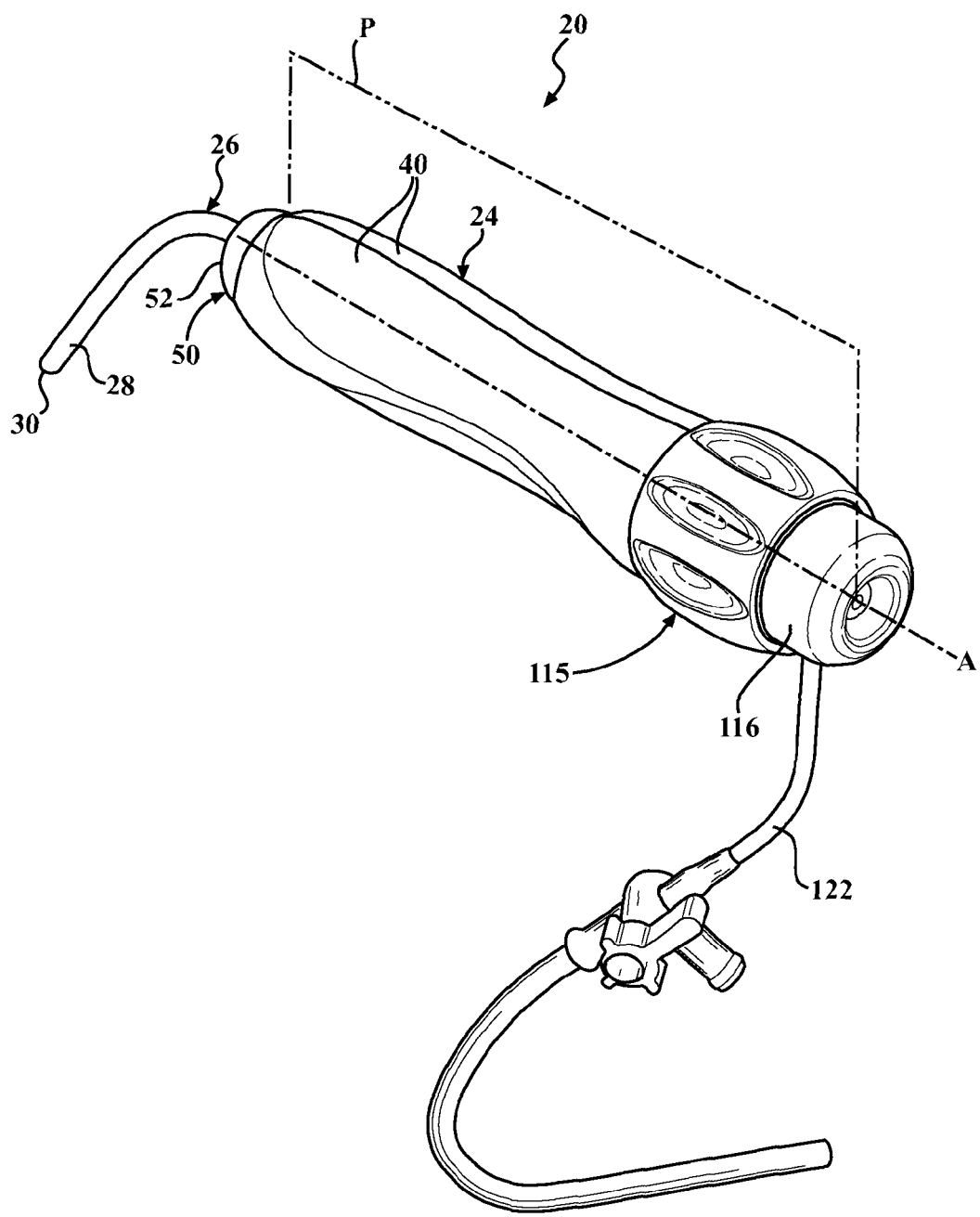
FIG. 1 is perspective assembled view of a modular handle assembly constructed in accordance with the principles of the present disclosure.

Example embodiments will now be described more fully with reference to the accompanying drawings. The example embodiments are provided so that this disclosure will be thorough and fully convey the scope to those skilled in the art. Numerous specific details are set forth such as examples of specific components, devices, mechanisms, assemblies and methods to provide a thorough understanding of various embodiments of the present disclosure. It will be apparent to those skilled in the art that specific details need not be employed, that example embodiments may be embodied in many different forms, and that neither should be construed to limit the scope of the disclosure. With this in mind, the present disclosure is generally directed to a modular handle assembly for supporting a controlling a steerable catheter.

Referring to the Figures, wherein like numerals indicate corresponding parts throughout the several views, a modular handle assembly 20, 120 is generally shown for supporting and controlling a steerable catheter 26 that has a tubular, flexible elongated body 28 that extends to a distal tip 30. At least one deflection wire 32 extends from the distal tip 30 of the steerable catheter 26 and through the body 28 for curling the distal tip 30 in response to movement of the deflection wire 32.

The modular handle assembly 20, 120 includes a handle 24 that has a ring shaped cross-section and which defines an inside surface 34 surrounding a hollow. However, the rear handle 24 could have a cross-section having another shape without departing from scope of the subject disclosure including, but not limited to, a square shape or rectangular shape. The handle 24 extends along an axis A from a proximal end 36 to a distal end 38 for being disposed about the body 28 of the steerable catheter 26.

The handle 24 includes a pair of halves 40 being mirror images with one another and mating along a plane P extending diametrically across the handle 24 though the axis A. A mechanical attachment 42, such as tabs, slots, nuts, bolts, or the like, removeably attach the halves 40 to one another at the plane P. The construction of the modular handle assembly 20, 120 having two halves 40 advantageously provides for ease in manufacturing and assembly of the modular handle 24 as the handle halves 40 can be molded separately. In addition, the two halves 40 provide for increased flexibility and modularity of the handle 24 assembly as components internal to the handle 24 can easily be installed while the halves 40 are disconnected from one another.

A plurality of flanges 44 extend inwardly in spaced and parallel relationship with one another from the inside surface 34 of each of the halves 40 of the handle 24 in the hollow for providing structural rigidity to the handle 24. It should be appreciated that any number of flanges 44 could be used to meet specific design needs and they could be oriented in other directions than shown in the Figures.

The handle 24 defines a proximal opening 46 about the axis A at the proximal end 36 and a distal opening 48 about the axis A at the distal end 38. A distal cap 50 is received by the distal opening 48. The distal cap 50 has a generally funnel shape and includes a mouth 52 that is disposed outside of the distal opening 48 of the handle 24. The distal cap 50 also includes a cylinder 54 that extends axially into the hollow of the handle 24 for receiving and engaging the body 28 of the steerable catheter 26 for tightening the handle 24 portion about the body 28 of the steerable catheter 26. The cylinder 54 has a thickness that can vary based on the diameter of the body 24 of the steerable catheter 22 to ensure that the front handle portion 32 is tightened about the body 24 of the steerable catheter 22. Put another way, the size of the cylinder 54 can be adjusted to accommodate a wide range of differently sized catheters 22, and thus provides for improved modularity of the subject handle assembly 20. It should be appreciated that the cylinder 54 could extend axially to various lengths to advantageously hold the body 24 of the steerable catheter 22 in place along different lengths based on operational needs.

Figure 2:
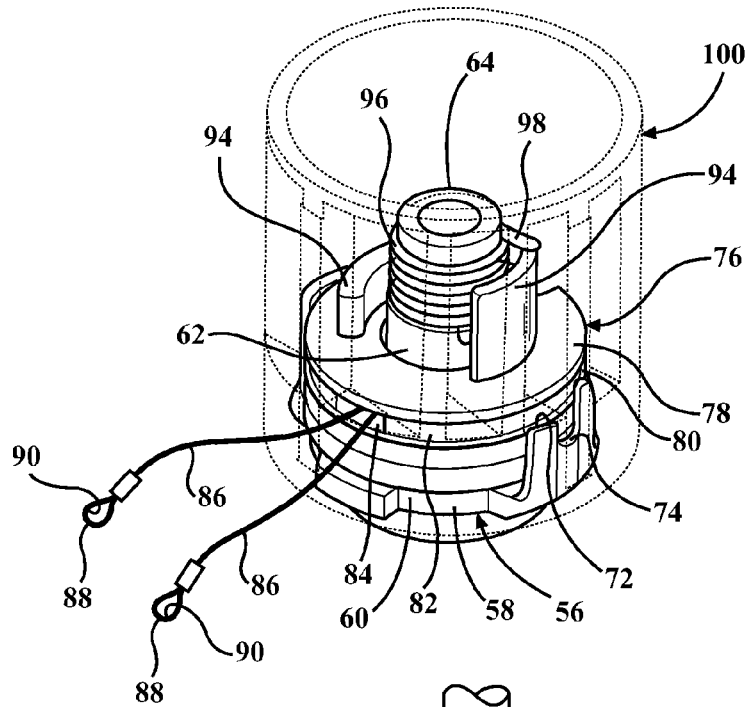
FIG. 2 is a perspective view of a frame, spindle, torsion spring, and guide cables of the modular handle assembly.
Figure 3:
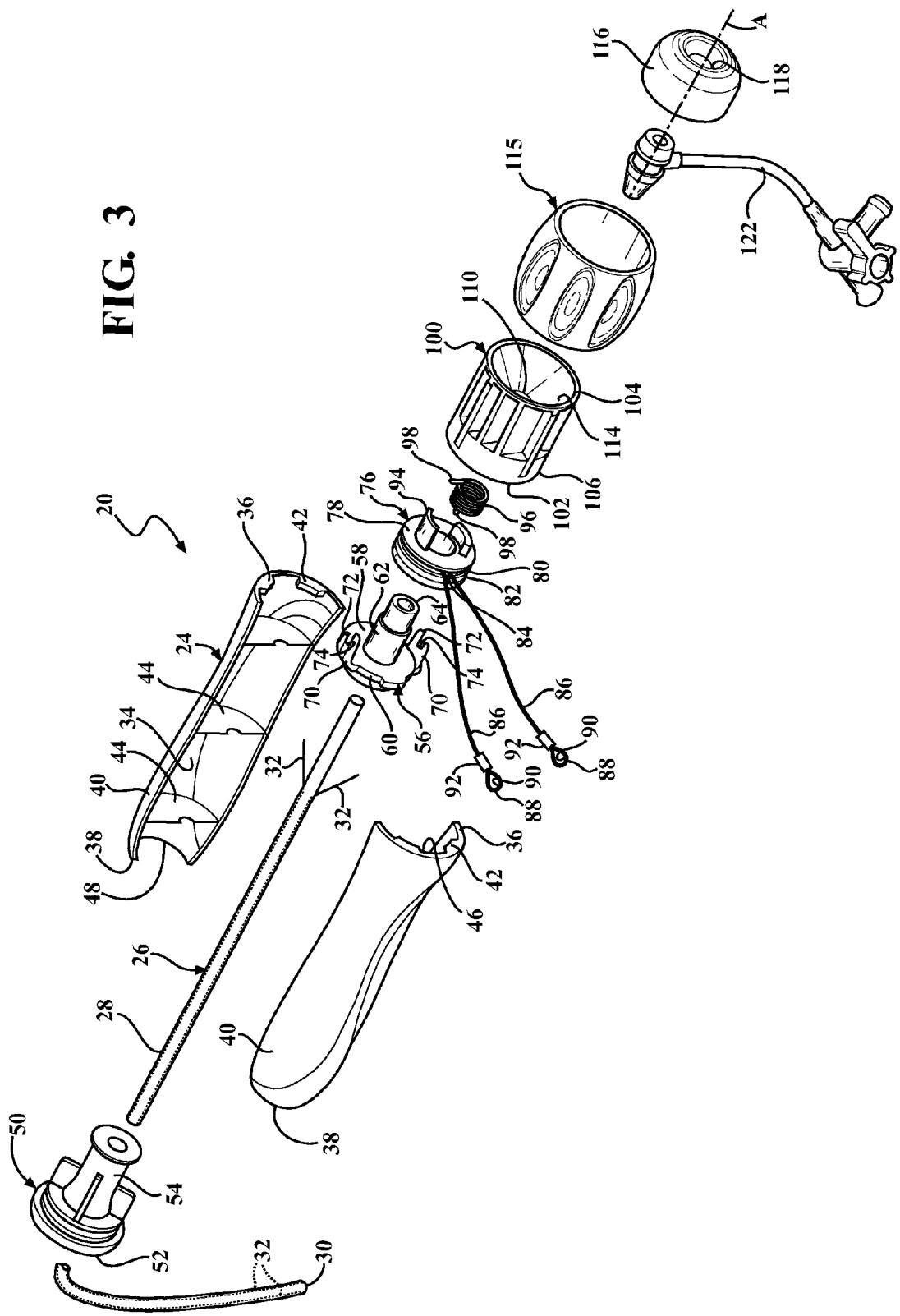
FIG. 3 is an exploded view of the assembled modular handle assembly illustrated in FIG. 1.

As best shown in FIGS. 2 through 3A, the modular handle assembly 20, 120 further includes a first frame 56 that includes a base 58 which has a disc shape and presents a perimeter 60 disposed about the axis A. The first frame 56 further includes a conduit 62 that has a tube shape and which extends through the base 58 along the axis A between a first termination 64 disposed outside of the handle 24 and a second termination 66 disposed in the hollow of the handle 24.

The first frame 56 further includes a plurality of support plates 68 that have a triangular shape and extend from the second termination 66 of the conduit 62 to the perimeter 60 of the base 58 for providing for structural rigidity of the first frame 56. The first frame 56 also includes a pair of arms 70 that extend axially from diametrically opposite sides of the perimeter 60 of the base 58 away from the hollow of the handle 24 and extending to an edge 72. Each of the arms 70 defines a groove 74 that extends axially from the edge 72 toward the base 58 of the first frame 56.

Figure 2A:
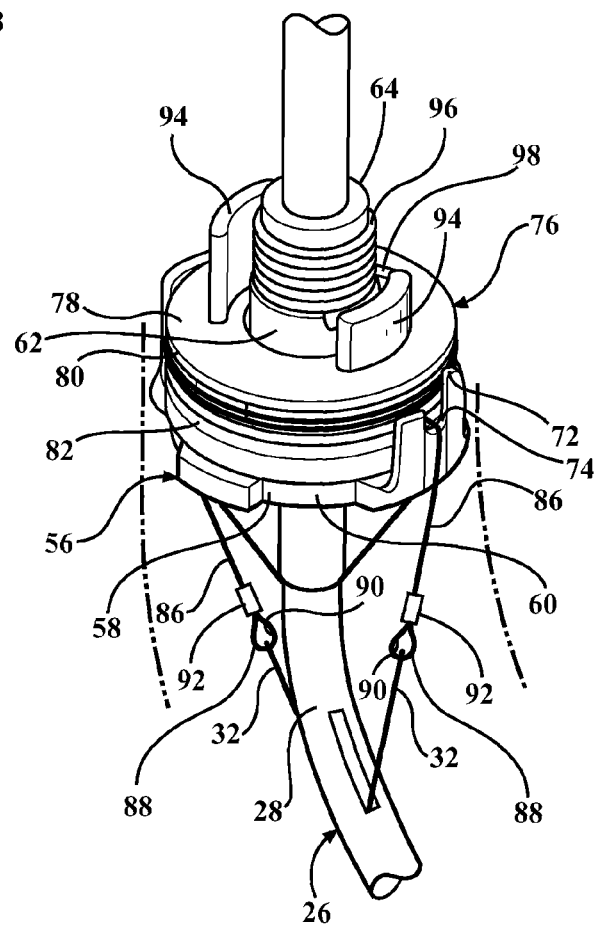
FIG. 2A is a side perspective view of the frame, spindle, torsion spring, and guide cables connected to deflection wires of a steerable catheter.

As best presented in FIGS. 2, 2A and 3B, the modular handle assembly 20 further includes a first spindle 76 that is rotatably disposed about the conduit 62 of the first frame 56. The first spindle 76 includes a platform 78 that has a washer shape and presents an outer periphery 80. The outer periphery 80 of the first spindle 76 defines a channel 82 that extends radially inwardly and about the periphery of the platform 78. The platform 78 of the first spindle 76 further defines a cavity 84 that extends radially inwardly from the channel 82.

A pair of first guide cables 86 each extend from an anchored end that is anchored in the cavity 84 of the platform 78 of the first spindle 76 to a distant end 88. Each of the first guide cables 86 are wrapped about the channel 82 of the platform 78 between the anchored and distant ends 88 and extend through one of the grooves 74 of the arms 70 to the distant end 88 in the hollow of the handle 24. The distant ends 88 of the first guide cables 86 connect with one of the deflection wires 32 of the steerable catheter 26 for axially moving the deflection wires 32 in response to rotation of the first spindle 76 about the conduit 62 of the first frame 56 to curl the distal tip 30 of the elongated body 28 of the steerable catheter 26 horizontally. The grooves 74 advantageously align the guide cables and space the guide cables from the first spindle 76. In a preferred arrangement, each of the first guide cables 86 of the first spindle 76 include a loop 90 at the distant end 88 for establishing the connection with one of the deflection wires 32. A crimp 92 is fixed partially about the loop 90 for securing the loop 90 in place.

The first guide cables 86 are wrapped around the channel 82 in opposite directions from one another for moving the first guide cables 86 in opposite directions from one another during rotation of the first spindle 76 about the first frame 56. Movement in this regard moves the deflection wires 32 in opposite directions from one another to allow the steerable catheter 26 to be curled in two horizontal or directly opposing directions. Thus, as can be understood from the aforementioned disclosure in connection with the Figures, as the first spindle 76 is rotated clockwise relative to the axis A, the wrapped first guide cables 86 cause simultaneous opposed displacement of the deflection wires 32. Specifically, because of opposing threaded relationship of the first guide cables 86 about the first spindle 76, one of the deflection wires 32 moves distally within the handle assembly 20 and the other of the deflection wires 32 moves proximally within the handle assembly 20 when the first spindle 76 is rotated clockwise relative to the handle 24. Conversely, when the first spindle 76 is rotated in a counterclockwise manner relative to the handle 24, each of the deflection wires 32 reverse or alternate their axial direction. Accordingly, the first spindle 76 of the first embodiment the modular handle assembly 20 provides for two (2) direction deflection of the distal end 26 of the catheter body 24.

A pair of projections 94 that have an arc shaped cross-section extend axially from the platform 78 of the first spindle 76 away from the handle 24 and radially adjacent to the conduit 62 of the first frame 56. Further, a torsion spring 96 is disposed about the conduit 62 of the first frame 56. The torsion spring 96 has a pair of fingers 98 that extend radially outwardly therefrom, with each of the fingers 98 of the torsion spring 96 engaging one of the projections 94 for biasing the first spindle 76 in a fixed position. Therefore, the first spindle 76 is naturally biased in the fixed position after rotation of the first spindle 76 about the conduit 62 of the frame.

A first barrel 100 that has a generally tube shape extends along the axis A between a lower rim 102 and an upper rim 104 and includes a wall 106 that extends between the lower rim 102 and the upper rim 104. The first barrel 100 is disposed about and is connected to the first spindle 76 for rotating the first spindle 76 about the conduit 62 in response to rotation of the first barrel 100 by a user of the modular handle assembly 20. The first barrel 100 further includes a step 108 that extends radially inwardly from the wall 106, as well as a duct 110 that extends along the axis A through the step 108. The duct 110 receives the body 28 of the steerable catheter 26. The first barrel 100 also defines a pair of indentations 112 that extend axially into the step 108 and which are disposed in axial alignment with one of the projections 94 of the first spindle 76. The indentations 112 receive the projections 94 of the first spindle 76 for connecting the first barrel 100 and the first spindle 76 and effectuating rotation of the first spindle 76 in response to rotation of the first barrel 100 about the axis A. The first barrel 100 further includes a cone 114 that extends radially inwardly from the upper rim 104 and axially toward the lower rim 102 to the duct 110. A first sleeve 115 that has a tube shape can be disposed about the wall 106 of the first barrel 100 for providing a gripping surface for operators of the steerable catheter 26. The first sleeve 115 includes an outside surface that could be made of various materials and could have different patterns or textures to provide for a satisfactory gripping surface for operators based on operational needs.

In the first enabling embodiment, as best presented in FIGS. 1 through 3B, the first frame 56 is removeably coupled with the proximal opening 46 of the handle 24 to close the proximal opening 46. Further, the first termination 64 of the first frame 56 is disposed outside of the handle 24 and the second termination 66 of the first frame 56 is disposed in the hollow of the handle 24. A proximal cap 116 that has a generally hemispherical shape is rotatably connected with the upper rim 104 and cone 114 of the first barrel 100. The proximal cap 116 defines a passageway 118 that extends therethrough along the axis A and is in fluid communication with the channel 82 for receiving and engaging the body 28 of the steerable catheter 26 for tightening the proximal cap 116 about the body 28 of the steerable catheter 26. The proximal cap 116 further defines an orifice 120 that extends radially inwardly therethrough for receiving a hose 122 of a stopcock assembly 22 of the steerable catheter 26.

Figure 5:
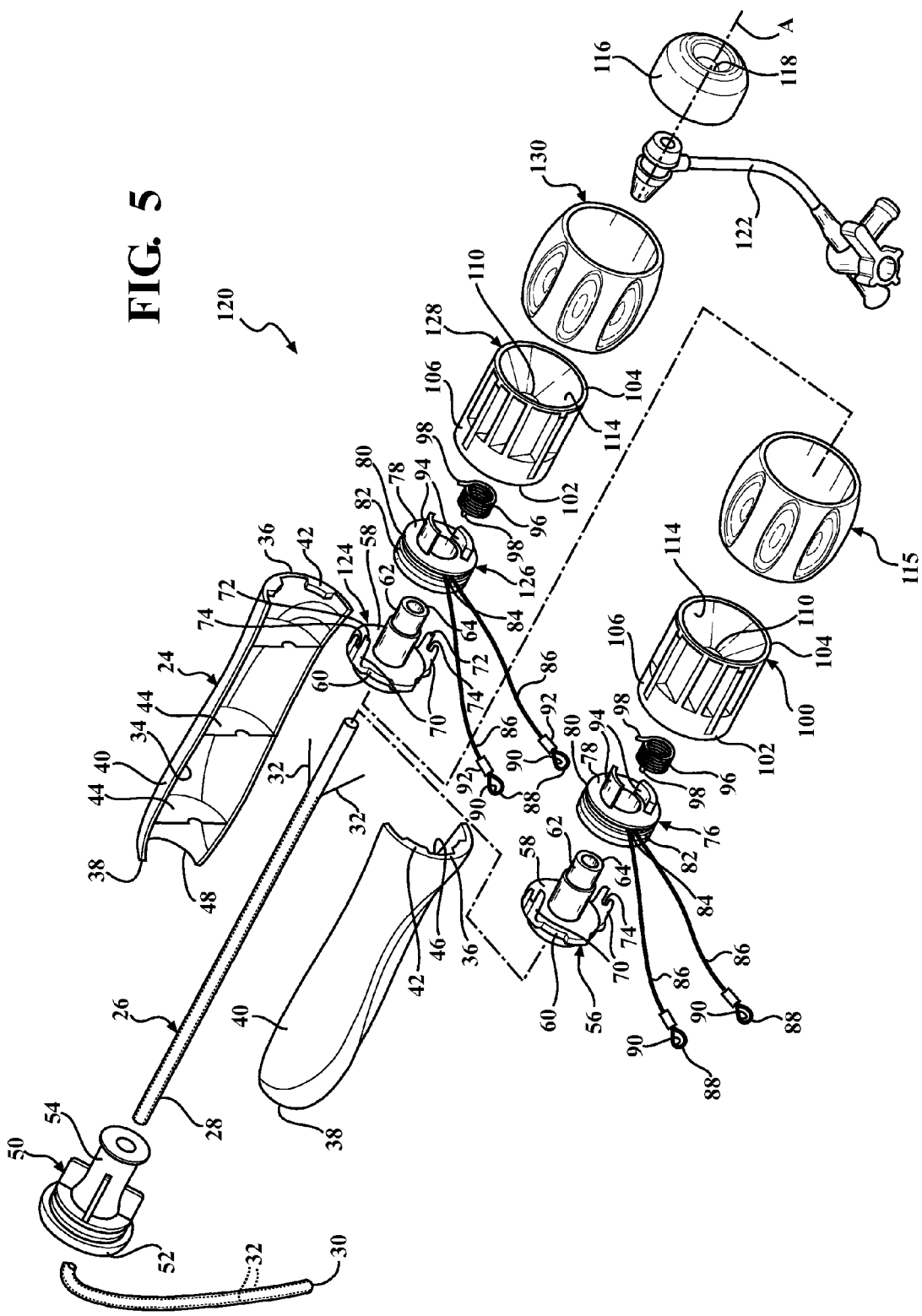
FIG. 5 is an exploded view of the assembled modular handle assembly illustrated in FIG. 5.
Figure 6:
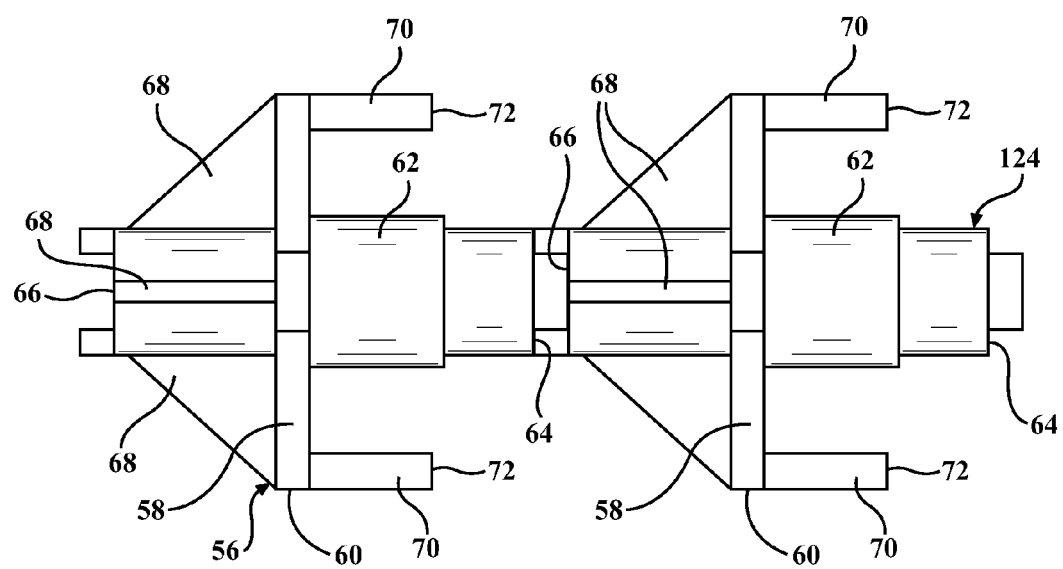
FIG. 6 is a side magnified view of a first spindle and second spindle of FIG. 5.

In a second enabling embodiment, as best presented in FIGS. 4-6, the modular handle assembly 120 further includes a second frame 124 that includes a base 58 that has a disc shape and which defines a perimeter 60 disposed about the axis A. The second frame 124 is removeably coupled with the proximal opening 46 of the handle 24 to close the proximal opening 46. The second frame 124 further includes a conduit 62 that has a tube shape that extends through the base 58 along the axis A. The conduit 62 of the second frame 124 extends between a first termination 64 disposed outside of the handle 24 and a second termination 66 that is disposed in the hollow of the handle 24. A mechanical connector fixedly connects the first termination 64 of the conduit 62 of the first frame 56 with the second termination 66 of the conduit 62 of the second frame 124 such that the conduits 62 of the first and second frames 56, 124 extend coaxially and in axial abutment with one another. The mechanical connector is comprised of a plurality of slot and legs that mate with one another, however other connections could be used like screws, nuts and bolts or the like.

The second frame 124 further includes a plurality of support plates 68 that have a triangular shape and which extend from the second termination 66 of the conduit 62 of the second frame 124 to the perimeter 60 of the base 58 for providing for structural rigidity of the second frame 124. The second frame 124 also includes a pair of arms 70 that extend axially from diametrically opposite sides of the perimeter 60 of the base 58 away from the hollow of the handle 24 and extend to an edge 72. Each of the arms 70 of the second frame 124 define a groove 74 that extends axially from the edge 72 toward the base 58 of the second frame 124.

As best shown in FIG. 5, in the second embodiment, a second spindle 126 is rotatably disposed about the conduit 62 of the second frame 124. The second spindle 126 includes a platform 78 that has a washer shape and presents an outer periphery 80. The outer periphery 80 of the second spindle 126 defines a channel 82 that extends radially inwardly and about the outer periphery 80 of the platform 78. The platform 78 of the second spindle 126 further defines a cavity 84 that extends radially inwardly from the channel 82.

A pair of second guide cables 87 each extend from an anchored end anchored in the cavity 84 of the platform 78 of the second spindle 126 to a distant end 88. The second guide cables 87 are wrapped about the channel 82 of the platform 78 between the anchored and distant ends 88 and extend through one of the grooves 74 of the arms 70 to the distant end 88 in the hollow of the handle 24. The distant ends 88 of the second guide cables 87 connect with one of the deflection wires 32 of the steerable catheter 26 for axially moving the deflection wires 32 in response to rotation of the second spindle 126 about the conduit 62 of the first frame 56 to curl the distal tip 30 of the elongated body 28 of the steerable catheter 26 in a direction that is transverse to the direction effectuated by the first spindle 76. The grooves 74 advantageously align the second guide cables 87 and space the second guide cables 87 from the second spindle 126. In a preferred arrangement, each of the second guide cables 87 of the second spindle 126 have a loop 90 at the distant end 88 for connecting with one of the deflection wires 32. A crimp 92 is fixed partially about the loop 90 for securing the loop 90 in place.

The second guide cables 87 are wrapped around the channel 82 in opposite directions from one another for moving the second guide cables 87 in opposite directions from one another during rotation of the second spindle 126 about the second frame 124. Comparably to the second guide cables 87 of the first spindle 76, movement in this regard moves the deflection wires 32 in opposite axial directions from one another to allow the steerable catheter 26 to be curled in two vertically or directly opposing directions. Thus, as can be understood from the aforementioned disclosure in connection with the Figures, as the second spindle 76 is rotated clockwise relative to the axis A, the wrapped second guide cables 87 cause simultaneous opposed displacement of the deflection wires 38 to which they are connected Specifically, because of opposing threaded relationship of the second guide cables 87 about the second spindle 126, one of the deflection wires 38 moves distally within the handle assembly 20 and the other of the deflection wires 38 moves proximally within the handle assembly 20 when the second spindle 126 is rotated clockwise relative to the handle 24. Conversely, when the first spindle 76 is rotated in a counterclockwise manner relative to the handle 24, each of the deflection wires 38 reverse or alternate their axial direction. Accordingly, the second spindle 126, in combination with the first spindle 76, provides for four (4) direction deflection of the distal end 26 of the catheter body 24. In addition, as can be understood from the aforementioned disclosure, the subject handle assembly 20 can be easily modified to incorporate the second spindle 126 to provide the four (4) direction deflection, and thus provides for more flexibility and modularity over the prior art handle assemblies. Further, the subject modular handle assembly 20 achieves the four (4) direction deflection of the distal end 26 of the catheter body 24 using less overall parts and a simpler design than the prior art handle assemblies.

A pair of projections 94 that have an arc shaped cross-section extend axially from the platform 78 of the second spindle 126 away from the handle 24 and radially adjacent to the conduit 62 of the second frame 124. Further, a torsion spring 96 is disposed about the conduit 62 of the second frame 124. The torsion spring 96 has a pair of fingers 98 that extend radially outwardly therefrom. Each of the fingers 98 of the torsion spring 96 engage one of the projections 94 for biasing the second spindle 126 in a fixed position for returning the second spindle 126 to the fixed position after rotation of the second spindle 126 about the conduit 62 of the second frame 124.

A second barrel 128 that has a generally tube shape extends along the axis A between a lower rim 102 and an upper rim 104 and includes a wall 106 that extends between the lower rim 102 and the upper rim 104. The second barrel 128 is disposed about and is connected to the second spindle 126 for rotating the second spindle 126 about the conduit 62 in response to rotation of the second barrel 128. The second barrel 128 further includes a step 108 that extends radially inwardly from the wall 106, and a duct 110 that extends along the axis A through the step 108. The second barrel 128 also defines a pair of indentations 112 that each extend axially into the step 108 in axial alignment with one of the projections 94 of the second spindle 126 and receive the projections 94 of the second spindle 126 for connecting the second barrel 128 and the second spindle 126. The second barrel 128 further includes a cone 114 that extends radially inwardly from the upper rim 104 and axially toward the lower rim 102 to the duct 110.

A second sleeve 130 that has a tube shape is disposed about the wall 106 of the second barrel 128 for providing a gripping surface for operators of the steerable catheter 26. Like the first sleeve 115, the second sleeve 130 includes an outside surface that could be made of various materials and could have different patterns or textures to provide for a satisfactory gripping surface for operators based on operational needs. A proximal cap 116 that has a generally hemispherical shape is rotatably connected with the upper rim 104 and the cone 114 of the second barrel 128. The proximal cap 116 defines a passageway 118 that extends therethrough along the axis A in fluid communication with the channel 82 for receiving and engaging the body 28 of the steerable catheter 26 for tightening the proximal cap 116 about the body 28 of the steerable catheter 26. The proximal cap 116 defines an orifice 120 that extends radially inwardly therethrough for receiving a hose 122 of a stopcock assembly 22 of the steerable catheter 26.

Due to the modular construction of modular handle assembly 20, additional spindles 76, 126, barrels 100, 126, and other aforementioned components could be added to the assembly 20 in the same fashion as the second enabling embodiment to provide for movement of the steerable catheter 22 in a wide variety other directions or along different lengths along the body 24 of the steerable catheter 22.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A modular handle assembly for supporting and controlling a steerable catheter having at least one deflection wire, said modular handle assembly comprising;
    a handle extending along an axis for being secured about a portion of the steerable catheter,
    at least one barrel rotatably connected to said handle for rotation about said axis,
    at least one spindle disposed in and connected with said at least one barrel for rotation about said axis with said at least one barrel,
    a frame including a base disposed about said axis and presenting a perimeter connected to said handle and a conduit extending from said base along said axis,
    said at least one spindle being rotatably disposed about said conduit of said frame,
    said frame including at least one arm extending axially from said base and extending to an edge which defines a groove,
    at least one guide cable extending from an anchored end being anchored to said at least one spindle and bending around said groove at approximately a 90 degree angle to overlay said at least one arm between said groove and said base for aligning and spacing said at least one guide cable from said at least one spindle,
    said at least one guide wire further extending from adjacent said base of said frame to a distant end for connection with the at least one of deflection wire of the steerable catheter,
    said at least one guide cable wrapped about said at least one spindle for axially moving the deflection wire in response to rotation of said at least one spindle about said axis by said barrel to curl the distal tip of an elongated body of the steerable catheter.

2. The modular handle assembly as set forth in claim 1, further comprising:
    wherein said at least one barrel includes a first barrel and a second barrel each rotatable connected to said handle for rotation about said axis,
    wherein said at least one spindle includes a first spindle and a second spindle axially aligned with one another, said first spindle disposed in and connected with said first barrel for rotation about said axis with said first barrel and said second spindle disposed in and connected with said second barrel for rotation about said axis with said second barrel, said at least one guide cable includes a first pair of guide cables and a second pair of guide cables,
    said first pair of guide cables wrapped about said first spindle in opposite directions relative to one another radial to said axis to move said first pair of guide cables in opposite directions from one another during rotation of said first spindle, and said second pair of guide cables wrapped about said second spindle in opposite directions relative to one another radial to said axis to move said second pair of guide cables in opposite directions from one another during rotation of said second spindle.

3. The modular handle assembly as set forth in claim 1 wherein said at least one guide cable includes a pair of guide cables wrapped about said at least one spindle in opposite directions relative to one another and radial to said axis to move said pair of guide cables in opposite directions from one another during rotation of said at least one spindle.

4. The modular handle assembly as set forth in claim 3 wherein said at least one arm includes a pair of arms extending axially from said base and extending to an edge.

5. The modular handle assembly as set forth in claim 4 wherein each of said arms defines a respective groove extending axially from said edge toward said base of said frame, and each of said guide cables bends around a respective one of said grooves at approximately a 90 degree angle to overlay a respective one of said sarm between said groove and said base for aligning said guide cables and spacing said guide cables from said at least one spindle.

6. The modular handle assembly as set forth in claim 5 wherein each of said arms extend from said base of said frame from diametrically opposite sides of said perimeter.

7. The modular handle assembly as set forth in claim 6 wherein said at least one spindle includes a platform having a washer shape disposed about said conduit of said frame and presenting an outer periphery.

8. A modular handle assembly for supporting and controlling a steerable catheter having at least a pair of deflection wires, said modular handle assembly comprising:

a handle extending along an axis for being secured about a portion of the steerable catheter, at least one barrel rotatably connected to said handle for rotation about said axis, at least one spindle disposed in and connected with said barrel for rotation about said axis with said barrel, a pair of guide cables each extending from an anchored end being anchored to said at least one spindle to a distant end for connection with one of the deflection wires of the steerable catheter, said pair of guide cables wrapped about said at least one spindle in opposite directions to one another radial to said axis to move said pair of guide cables in opposite directions from one another during rotation of said at least one spindle for moving the deflection wires and curling the distal tip of an elongated body of the steerable catheter, a frame including a base disposed about said axis and presenting a perimeter connected to said handle and a conduit extending from said base along said axis, said at least one spindle being rotatably disposed about said conduit of said frame, said frame further including a pair of arms extending axially from said base and extending to an edge, each of said arms defining a groove extending axially from said edge toward said base of said frame for receiving one of said guide cables to align said guide cables and space said guide cables from said at least one spindle, each of said arms extending from said base of said frame from diametrically opposite sides of said perimeter, said at least one spindle including a platform having a washer shape disposed about said conduit of said frame and presenting an outer periphery, and said outer periphery of said at least one spindle defining a channel that extends radially inwardly and annularly about said outer periphery of said platform.

9. The modular handle assembly as set forth in claim 8 wherein said platform of said at least one spindle further defines a cavity extending radially inwardly from said channel.

10. The modular handle assembly as set forth in claim 9 wherein said guide cables each extend from an anchored end anchored in said cavity of said platform of said spindle to a distant end.

11. The modular handle assembly as set forth in claim 10 wherein said guide cables are each wrapped about said channel of said platform between said anchored and distant ends and extend through one of said grooves of said arms to said distant end for connecting with one of the deflection wires of the steerable catheter.

12. A modular handle assembly for supporting and controlling a steerable catheter having at least a pair of deflection wires, said modular handle assembly comprising:

a handle extending along an axis for being secured about a portion of the steerable catheter, at least one barrel rotatably connected to said handle for rotation about said axis, at least one spindle disposed in and connected with said barrel for rotation about said axis with said barrel, a pair of guide cables each extending from an anchored end being anchored to said at least one spindle to a distant end for connection with one of the deflection wires of the steerable catheter, said pair of guide cables wrapped about said at least one spindle in opposite directions to one another radial to said axis to move said pair of guide cables in opposite directions from one another during rotation of said at least one spindle for moving the deflection wires and curling the distal tip of an elongated body of the steerable catheter, a frame including a base disposed about said axis and presenting a perimeter connected to said handle and a conduit extending from said base along said axis, said at least one spindle rotatably disposed about said conduit of said frame, said frame further including a pair of arms extending axially from said base and extending to an edge, each of said arms defining a groove extending axially from said edge toward said base of said frame for receiving one of said guide cables to align said guide cables and space said guide cables from said at least one spindle, each of said arms extending from said base of said frame from diametrically opposite sides of said perimeter, said at least one spindle including a platform having a washer shape disposed about said conduit of said frame and presenting an outer periphery, and at least one projection extending axially from said platform of said at least one spindle.

13. The modular handle assembly as set forth in claim 12 wherein said at least one projection includes a pair of projections having an arc shape.

14. The modular handle assembly as set forth in claim 13, further including a torsion spring disposed about said conduit of said frame and having a pair of fingers extending radially outwardly therefrom each in engagement with one of said projections for biasing said at least one spindle in a fixed position for returning said at least one spindle to said fixed position after rotation of said at least one spindle about said conduit of said frame.

15. The modular handle assembly as set forth in claim 14 wherein said barrel has a generally tube shape and presents a wall disposed about and connected to said at least one spindle for rotating said at least one spindle about said conduit in response to rotation of said barrel.

16. The modular handle assembly as set forth in claim 15 wherein said at least one barrel further includes a step extending radially inwardly from said wall.

17. The modular handle assembly as set forth in claim 16 where said at least one barrel includes a duct defined by said step and extending along said axis for receiving the body of the catheter.

18. The modular handle assembly as set forth in claim 17 wherein said at least one barrel defines a pair of indentations each extending axially into said step and disposed in axial alignment with one of said projections of said at least one spindle and receiving said projections of said at least one spindle for connecting said at least one barrel and said at least one spindle.

19. The modular handle assembly as set forth in claim 18 and further including a sleeve disposed about said wall of said at least one barrel and connected with said at least one barrel for providing a gripping surface for operators of the steerable catheter.

\* \* \* \* \*